United States Patent [19]

Blumenfeld et al.

[11] Patent Number: 5,042,482
[45] Date of Patent: Aug. 27, 1991

[54] DISPOSABLE MONOPOLAR NEEDLE ASSEMBLY

[75] Inventors: Arthur Blumenfeld, Brewster, N.Y.; Bert D. Heinzelman, North Bergen, N.J.; Jeffrey Stein, Miford, Conn.

[73] Assignee: Medelec, Inc., Pleasantville, N.Y.

[21] Appl. No.: 552,838

[22] Filed: Jul. 16, 1990

Related U.S. Application Data

[63] Continuation of Ser. No. 310,098, Feb. 14, 1989, abandoned.

[51] Int. Cl.⁵ .............................................. A61B 5/492
[52] U.S. Cl. .................................................. 128/642
[58] Field of Search ....................... 128/642, 733, 741; 606/44, 49, 50

[56] References Cited

U.S. PATENT DOCUMENTS

| 861,159 | 7/1907 | Burch . | |
|---|---|---|---|
| 1,863,118 | 6/1932 | Liebel . | |
| 3,035,580 | 5/1962 | Guiorguiev | 128/303.18 |
| 3,144,018 | 8/1964 | Head | 128/642 |
| 3,313,293 | 4/1967 | Chesebrough et al. | 128/733 X |
| 3,597,582 | 8/1971 | Goode et al. | 219/144 |
| 3,920,022 | 11/1975 | Pastor | 128/303.13 |
| 4,014,343 | 3/1977 | Esty | 606/49 X |
| 4,032,738 | 6/1977 | Esty et al. | 200/157 |
| 4,037,590 | 7/1977 | Dohring et al. | 128/24.4 |
| 4,062,353 | 12/1977 | Foster et al. | 128/1.1 |
| 4,185,619 | 1/1980 | Reiss | 128/1.1 |
| 4,240,421 | 12/1980 | Carr | 128/215 |
| 4,295,467 | 10/1981 | Mann et al. | 606/44 |
| 4,343,308 | 8/1982 | Gross | 128/303.13 |

FOREIGN PATENT DOCUMENTS

2177309A  1/1987  United Kingdom ........... 128/303.13

OTHER PUBLICATIONS

Pollack, Med & Biol. Eng., vol. 9, No. 6, Nov. 1971, p. 658.

Primary Examiner—Lee S. Cohen
Attorney, Agent, or Firm—Charles E. Baxley

[57] ABSTRACT

A monopolar needle assembly comprises a disposable insulated needle having an uninsulated tip projecting from a needle stem and a sheath for covering the needle. A brass connector pin is connected to the needle stem of the electrically conductive needle. A handle is provided for supporting the connector pin and for holding the needle when the needle is inserted into a patient or the like. The connector pin, which is housed within the handle, is secured to a detachable power cord.

16 Claims, 2 Drawing Sheets

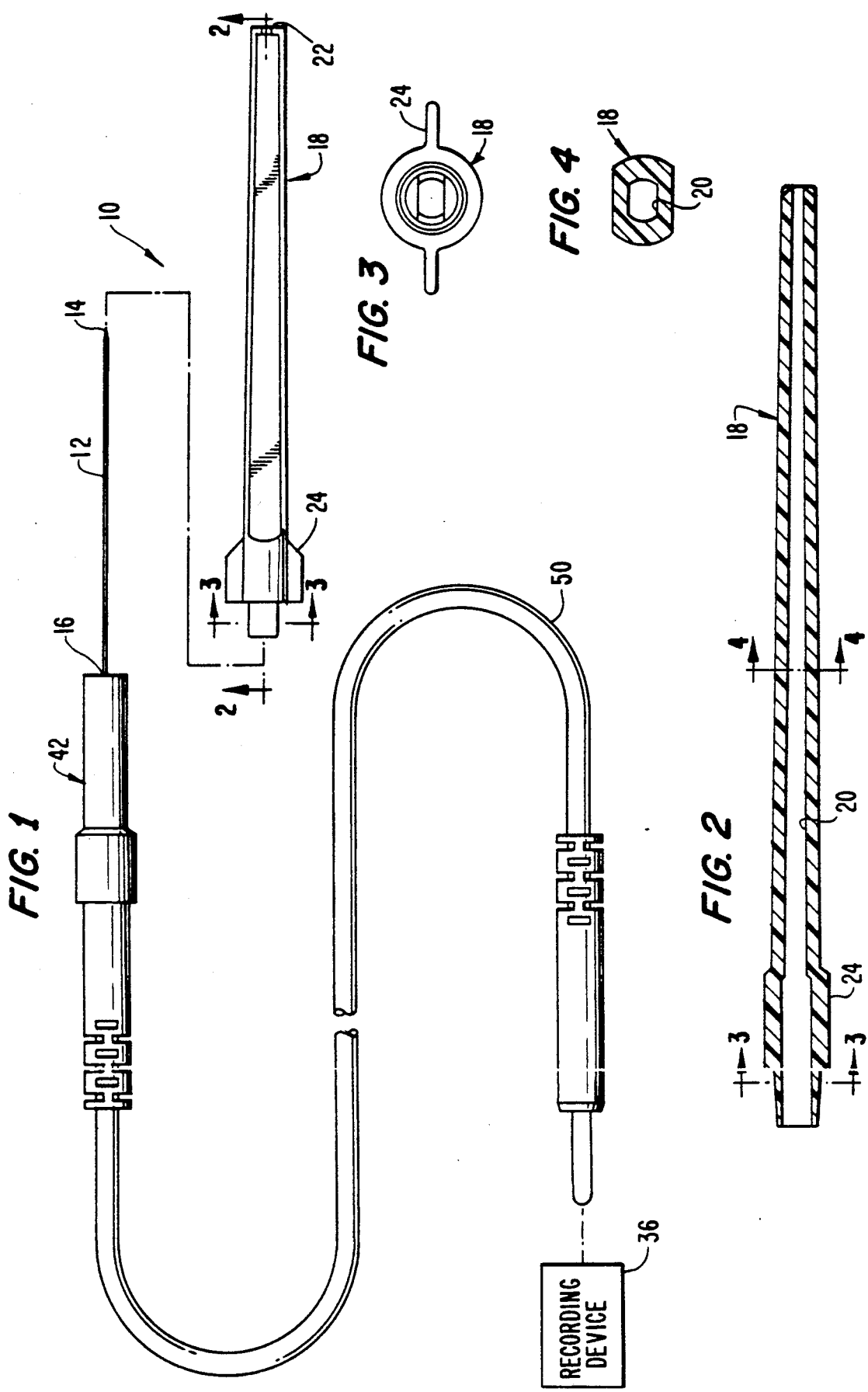

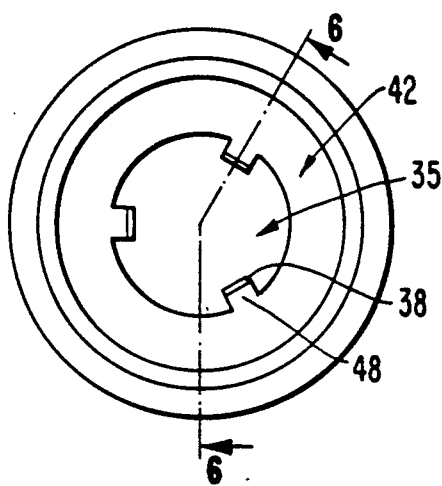
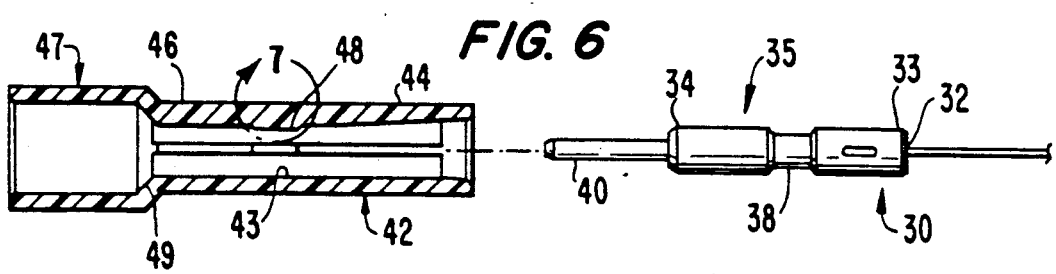
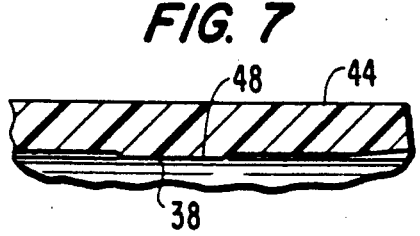
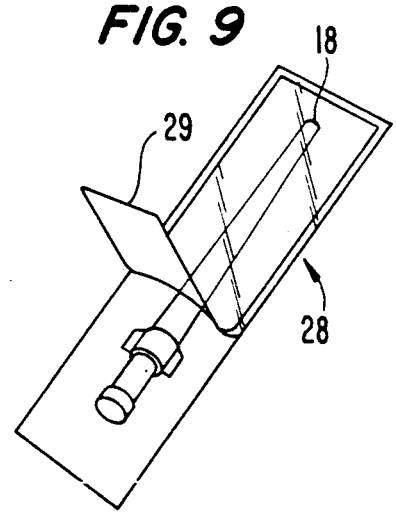
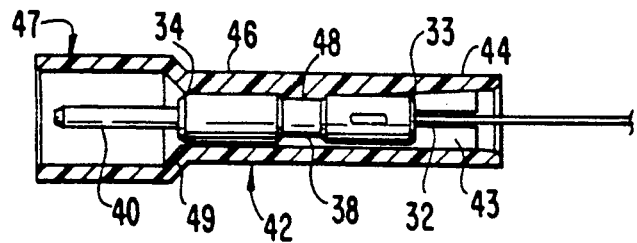

5,042,482

1

DISPOSABLE MONOPOLAR NEEDLE ASSEMBLY

This application is a continuation of application Ser. No. 07/310,098, filed Feb. 14, 1989, now abandoned.

BACKGROUND OF THE INVENTION

The present invention relates to a disposable monopolar needle assembly and, more particularly, to a disposable monopolar needle assembly having a detachable cord.

Monopolar needles have been found to have important medical applications. Indeed, monopolar needles enable detection of electrical activity in muscle fiber. As a result, such needles have been used in conjunction with neurophysiological recording systems to record, and thereby, diagnose a wide range of muscular and neurological disorders.

Certain conventional monopolar needles contain an insulated needle with an uninsulated tip. The exposed tip affords a relatively small surface area for detecting electrical activity when inserted within a patient. Unfortunately, however, the insulating coating has a tendency to wear away from the tip through continued use of the needle. Variation in tip exposure from wear along the insulated needle distorts the shape of the recorded waveforms. Moreover, such needles present a risk of transmitting diseases from patient to physician or others when the needle is prepared for sterilization.

SUMMARY OF THE INVENTION

Accordingly, it is an object of the present invention to provide a monopolar needle assembly which is disposable. This insures an accurate waveform recording since the tip exposure of each new needle is consistent. The disposability of the needle also eliminates re-sterilization and re-use, thereby reducing the risk of transmitting diseases from the patient to individuals handling the needle, such as when the needle is prepared for sterilization.

Another object of the present invention is to provide a radiation resistant, monopolar needle assembly which is suitable for sterilization by gamma radiation. The monopolar needle assembly of the present invention has a two-piece construction, making it unnecessary to throw out the entire needle assembly after use.

An additional object of the present invention is to provide a monopolar needle assembly which has an insertion tip consistent in size, thereby improving the diagnostic yield of the needle assembly.

A still further object of the present invention is to provide a new and improved monopolar needle assembly that is inexpensive, not complicated, and easy to assemble.

It is a further object of this invention to provide a monopolar needle assembly having a detachable cord, thereby enhancing the overall utility and accessibility of the needle assembly.

Additional objects and advantages of the invention will appear in the following description, and other objects and advantages will be obvious from that description. The stated objects and advantages of the invention may be realized by the apparatus and methods particularly pointed out in the appended claims.

To achieve the foregoing objects, and in accordance with the purposes of the invention as embodied and broadly described herein, the monopolar needle assembly of this invention comprises a disposable, electrically conductive needle having an insertion tip projecting from a needle stem. A brass connector pin is secured to the needle stem of the disposable needle. Handle means supports the connector pin and holds the disposable needle for insertion into a patient or the like. The handle means includes a hollow, elongated housing having an interior surface. The housing engages the connector pin along the interior surface for rigidly connecting the disposable needle to the handle means. An elongated sheath covers the needle and is releasably attached to the handle means. The monopolar needle assembly further includes means for electrically connecting the connector pin to a recording system.

The accompanying drawings, which are incorporated in and constitute a part of the specification, illustrate one embodiment of the invention and, together with the summary description given above and the detailed description given below, serve to explain the principles of the invention.

BRIEF DESCRIPTION OF THE DRAWINGS

FIG. 1 is an exploded view of the monopolar needle assembly of the present invention;

FIG. 2 is a cross-sectional view of a sheath taken along line 2—2 of FIG. 1;

FIG. 3 is a bottom view of a flanged end of the sheath shown in FIGS. 1 and 2 and taken across line 3—3 of FIG. 2;

FIG. 4 is a cross-sectional view of the sheath taken along line 4—4 of FIG. 2;

FIG. 5 is an end elevational view of a handle shown in FIG. 1;

FIG. 6 is an exploded view of the handle and a connector pin normally disposed within the handle, the handle being viewed in cross-section along line 6—6 of FIG. 5;

FIG. 7 is an expanded view of ribs disposed along a hollow portion of the handle encircled in FIG. 6;

FIG. 8 is a cross-sectional view of the handle of FIG. 6, in which the connector pin is depicted to be disposed within the housing; and FIG. 9 is a plastic pouch for retaining the monopolar needle assembly of the present invention prior to use.

DESCRIPTION OF THE PREFERRED EMBODIMENTS

Reference will now be made in detail to a presently preferred embodiment of the present invention, examples of which are illustrated in the accompanying drawings.

A preferred embodiment of the monopolar needle assembly of the present invention is shown in FIG. 1 and identified generally by reference numeral 10. As embodied herein, the monopolar needle assembly 10 comprises an electrically conductive needle 12 for insertion into a patient. The needle 12 includes an insertion tip 14 projecting from a needle stem 16. Preferably, needle 12 is made of an electrically conductive material such as stainless steel. Needle stem 16 is insulated for its entire length.

In accordance with the present invention, the monopolar needle is disposable, and is therefore designed for one time use to insure the needle is always properly sterilized. Accordingly, the needle 12 is radiation resistant and is not capable of being autoclaved, so that it cannot be re-sterilized and re-used. As a result, the needle 12 may be discarded and replaced with another needle after each use. Therefore, the needle 12 always affords consistent tip exposure with each use.

As embodied herein and shown in FIGS. 1 and 2, the present invention includes a protective sheath for covering the needle. The protective sheath, which is identified generally by reference numeral 18, is preferably plastic and injection molded. The needle 12 is disposed within a protective sheath 18 until the needle is inserted into the patient, thereby preventing contamination of the needle. Moreover, the needle 12 is not resheathable, thus preventing re-use and further sterilization of the needle.

As embodied herein, the exterior and interior surfaces of the protective sheath 18 are tapered to conform essentially to the elongated configuration of the needle 12. As shown in FIGS. 3 and 4, an interior surface 20 of the sheath 18 is quasirectangular in cross-section, with two of the sides being rounded. The exterior of sheath 18 adjacent insertion tip 14 of needle 12 is formed with beveled notches 22. The portion of the sheath proximate needle stem 16 includes flanges 24 projecting from the exterior of the sheath 18. Flanges 24 prevent the monopolar needle assembly of the present invention from rolling if it is dropped.

In accordance with the present invention, the sheath is housed in a nonreusable package. As shown in FIG. 9, a package, shown generally at 28, includes a clear plastic pouch 29 enabling the sheath 18 to be viewed within package 28. The sheath 18 is also made of a translucent plastic material so that the needle length can thus be seen through the package before the package is opened. The package 28 and the sheath 18 minimize handling of monopolar needle assembly 10 before each use, thereby minimizing the risk of contamination of the needle 12.

As embodied herein and shown principally in FIGS. 6 and 8, the present invention includes a connector pin, which is identified generally by reference numeral 30. The connector pin 30 is connected to the needle stem 16 of the disposable needle 12. Preferably, the connector pin 30 is a substantially cylindrical electrode. According to the present invention, the needle 12 is secured to the connector pin 30. For example, the needle 12 may be crimped into the pin 30. Also, the stem 16 of the needle 12 may be mounted within a knurled (not shown) aperture 32. Any other conventional methods, such as soldering, also may be used to securely mount the needle 12 on the connector pin 30.

As embodied herein, the connector pin 30 includes a connector body shown generally at 35. The connector body 35 has a needle-receiving end 33 and a conductor end 34. Needle-receiving end 33 receives needle stem 16. Connector body 35 is recessed in the middle as shown at 38, for reasons discussed hereinafter. Conductor end 34 includes a probe 40 extending away from the connector body 35. The probe 40 connects the connector pin 30 ultimately to a recording device 36. Typically, the probe 40 is 0.040 inches in diameter and mates with a standard electronic 0.040 female connector in recording device 36. The next smallest section, recessed section 38, is typically 0.065 inches in diameter.

As embodied and broadly described herein, the present invention includes handle means for supporting the connector pin and for holding the disposable needle when inserting the needle into a patient or the like. The handle means includes a hollow housing shown generally at 42 having an interior surface 43. The housing 42 is preferably formed of plastic and includes a needle portion 44 for housing needle-receiving end 33 of the connector body 35. The housing 42 also includes a conductor portion 46 extending from the needle portion 44. The conductor portion 46 houses a conductor end 34 of the connector body 35. Finally, the housing 42 includes a probe portion 47 for housing probe 40. The probe portion 47 serves as a centering device to facilitate lining up the female connector on the recording device 36 with the conductor body 35 housed in conductor portion 46. In addition, the probe portion 47 is connected to a conductor portion 46 by shoulders 49. The shoulders 49 form a stop so that when needle 12 is withdrawn from the patient the chance that the physician will lose his grip on the needle is considerably lessened.

The sheath 18 is releasably attached to the needle portion 44 of the housing 42. Interior surface 43 of housing 42 is tapered in the shape of a frustum so that it decreases in diameter as it extends rearwardly, and the exterior surface of sheath 18 is tapered in the shape of a complementary frustum so that it decreases in diameter as it extends rearwardly. This arrangement allows the sheath 18 and the handle housing 42 to mate together with an interference fit. It is this interference with the resultant distortion of the plastic of sheath 18 that keeps the sheath and the handle means together.

The needle portion of the housing also includes engagement means for securely holding the connector pin within the housing, and for rigidly connecting the disposable needle to the handle means. As shown in FIGS. 6 and 7 in particular, the engagement means includes a plurality of radially extending ribs 48. Ribs 48 engage recessed section 38 of connector body 35 to secure the connector pin 30 in handle housing 42. The connector pin 30 is press-fit onto the interior surface 43 of the handle housing 42 until the ribs 48 mate with the recessed section 38.

In addition, the recessed section 38 provides further advantages for the connector pin 30. For example, the recessed section 38 reduces the amount of material that has to be moved when the needle 12 is crimped into pin 30. Also, the recessed section 38 serves as the female part or mortise into which the male part or tenon of handle housing 42 locks. This prevents the needle assembly from slipping back and forth in the plastic handle housing as the physician moves the needle in and out of the patient. This feature is important because the physician moves the needle in increments as small as 0.001 inch. Consequently, there must not be any motion of the needle relative to the handle as the physician moves the needle.

In accordance with the present invention, there is also provided a means for electrically connecting the connector pin to the recording device The means for electrically connecting the connector pin to the recording device includes a flexible electrical cord 50 as shown in FIG. 1. The cord 50 is detachably connected to the probe 40 of the connector pin 30 at one end. The other end of the cord 50 is connected to recording device.

In operation, a user, such as a physician, removes a sterile package 28 from the needle assembly 10 and removes the needle assembly from the package The physician connects the flexible cord 50 to the recording device 36 and removes the sheath 18 from the needle 12. The physician then inserts the insertion tip 14 of the needle 12 into the patient. After the physician is done testing the patient he removes the needle from the patient. The physician then places the entire needle assembly into a "V" shaped hole in a disposed container, such as a Sharps container. By pulling the flexible cord 50 needle 12 separates from connector pin 30. The needle drops into the container for easy disposal, without the physician ever having to handle the needle. The monopolar needle assembly of the present invention thereby reduces the risk of transmitting diseases from the patient to the physician via the needle.

Additional advantages and modifications will readily occur to those skilled in the art. The invention in its broader aspects is, therefore, not limited to the specific details, representative apparatus, and illustrative examples shown and described. Accordingly, departures may be made from such details without departing from the spirit or scope of the general inventive concept as defined by the appended claims and their equivalents.

What is claimed is:

1. A monopolar needle assembly comprising:
   a disposable needle having an insertion tip projecting from a needle stem;
   a brass connector pin secured to said needle stem of said disposable needle;
   handle means for supporting said connector pin and for holding said disposable needle, said handle means including a hollow, elongated housing having an interior surface for receiving said connector pin, said housing engaging said connector pin along said interior surface, thereby rigidly connecting said disposable needle to said handle means;
   flexible cord means for electrically connecting said connector pin to a recording device, said cord means being detachably connected to the connector pin; and
   protective means releasably attached to said handle means for covering the needle to maintain sterility of the needle before insertion.

2. The monopolar needle assembly of claim 1, wherein said protective means includes an elongated sheath having an interior surface tapered to conform substantially to said needle.

3. The monopolar needle assembly of claim 2, wherein said sheath includes beveled notches proximate said insertion tip.

4. The monopolar needle assembly of claim 2, wherein said sheath includes flanges substantially adjacent said handle means.

5. The monopolar needle assembly of claim 1, wherein said brass connector pin is press-fit onto said interior surface.

6. The monopolar needle assembly of claim 1, wherein said connector pin includes a substantially cylindrical body having a recessed section.

7. The monopolar needle assembly of claim 6, wherein said housing includes engagement means extending along said interior surface for rigidly connecting said disposable needle to said handle means.

8. The monopolar needle assembly of claim 7, wherein said engagement means includes radially extending ribs for engaging said recessed section.

9. The monopolar needle assembly of claim 1, wherein said protective means includes means for attaching said protective means to said handle means.

10. The monopolar needle assembly of claim 9, wherein said attaching means comprises a member in the shape of a frustum, said member engaging a correspondingly shaped portion on the handle means to establish an interference fit therebetween.

11. A monopolar needle assembly comprising:
    a disposable needle having an insertion tip projecting from a needle stem;
    sheath means for covering the needle, said sheath means including an elongated, hollow member tapered to conform substantially to said needle, said sheath means having flanges at a first end which fits over said needle stem;
    a brass connector pin secured to said needle stem of said disposable needle, said connector pin including a needle-receiving end and a conductor end, said conductor end having a conductor probe for connecting said needle to a recording device, said connector pin having a connector body extending between said needle-receiving end and said conductor end;
    a handle for supporting said connector pin and for holding said disposable needle, said handle including a hollow housing having an interior surface for receiving said connector pin, said housing including a needle portion and a conductor portion, said needle-receiving end projecting within said needle portion and said conductor end projecting within said conductor portion, said needle portion including engagement means for securely holding said connector pin within said housing; and
    a flexible power cord electrically connecting said connector pin to said recording device, said flexible power cord being detachably connected to the connector pin.

12. The monopolar needle assembly of claim 11, wherein said engagement means includes radially extending rib means for engaging a middle section of said connector pin.

13. The monopolar needle assembly of claim 11, wherein said brass connector pin is press-fit onto said interior surface of said housing.

14. The monopolar needle assembly of claim 11, wherein said sheath means includes beveled notches at an end distal said first end.

15. The monopolar needle assembly of claim 11, wherein said sheath means includes means for attaching said sheath means to said handle.

16. The monopolar needle assembly of claim 15, wherein said attaching means comprises a member in the shape of a frustum positioned adjacent said flanges, said member engaging a correspondingly shaped portion on the handle to establish an interference fit therebetween.

* * * * *